United States Patent [19]

Mourkidou et al.

[11] Patent Number: 5,431,157
[45] Date of Patent: Jul. 11, 1995

[54] ANESTHESIA CONDUIT

[76] Inventors: Sotiria Mourkidou, 27112 Malibu Cove Colony Dr., Malibu, Calif. 90265; William J. Binder, 9201 Sunset Blvd., Suite 809, Los Angeles, Calif. 90069

[21] Appl. No.: 186,725

[22] Filed: Jan. 25, 1994

[51] Int. Cl.⁶ .......................................... A61M 39/10
[52] U.S. Cl. .......................... 128/203.12; 128/207.14; 128/911; 128/912; 128/DIG. 26
[58] Field of Search .................. 128/203.12, 911, 912, 128/DIG. 26, 207.14

[56] References Cited

U.S. PATENT DOCUMENTS

| | | |
|---|---|---|
| 4,007,737 | 2/1977 | Paluch .................. 128/911 |
| 4,621,634 | 11/1986 | Nowacki et al. |
| 4,637,384 | 1/1987 | Schroeder |
| 4,838,255 | 6/1989 | Lambert |
| 4,852,563 | 8/1989 | Gross .................. 128/912 |
| 4,852,564 | 8/1989 | Sheridan .................. 128/912 |
| 4,909,248 | 3/1990 | McLennan Anderson |
| 4,953,547 | 9/1990 | Poole, Jr. |
| 4,967,743 | 11/1990 | Lambert |
| 4,987,895 | 1/1991 | Hemlich |
| 5,042,470 | 8/1991 | Kanesaka .................. 128/204.18 |
| 5,062,420 | 11/1991 | Levine .................. 128/DIG. 26 |
| 5,065,754 | 11/1991 | Jensen .................. 128/912 |
| 5,101,817 | 4/1992 | Etter .................. 128/DIG. 26 |
| 5,121,746 | 6/1992 | Sikora .................. 128/203.12 |
| 5,181,508 | 1/1993 | Poole, Jr. |

Primary Examiner—Edgar S. Burr
Assistant Examiner—William J. Deane, Jr.
Attorney, Agent, or Firm—Spensley Horn Jubas & Lubitz

[57] ABSTRACT

An anesthesia conduit for connecting a tracheal tube and a gas circuit. The connector includes a flexible portion integral with a substantially rigid longitudinally extending portion. The longitudinally extending portion may include two ports, one connected to apparatus such as an respiratory gas monitor, and the other configured such that suction catheters can be inserted into the conduit and tracheal tube.

18 Claims, 2 Drawing Sheets

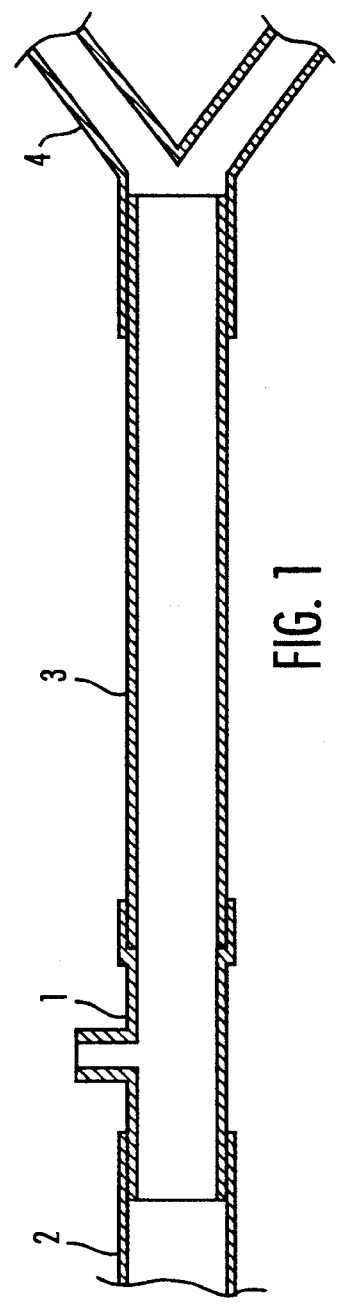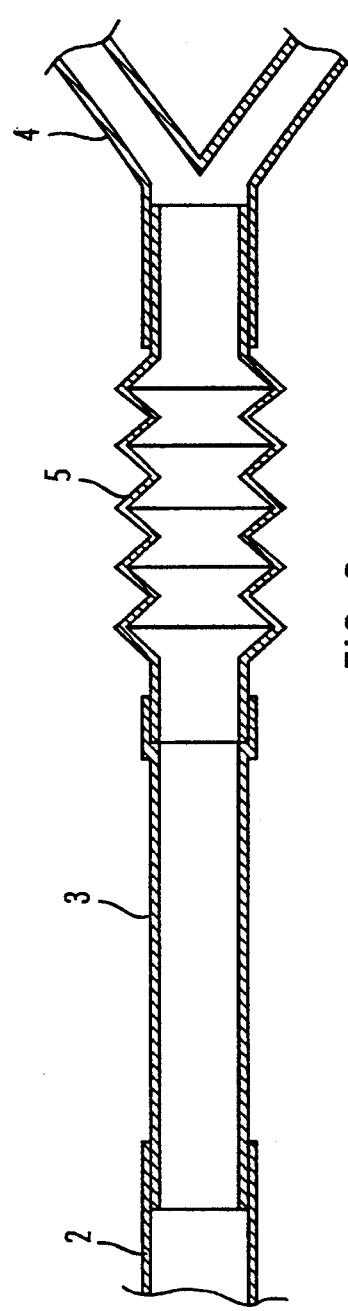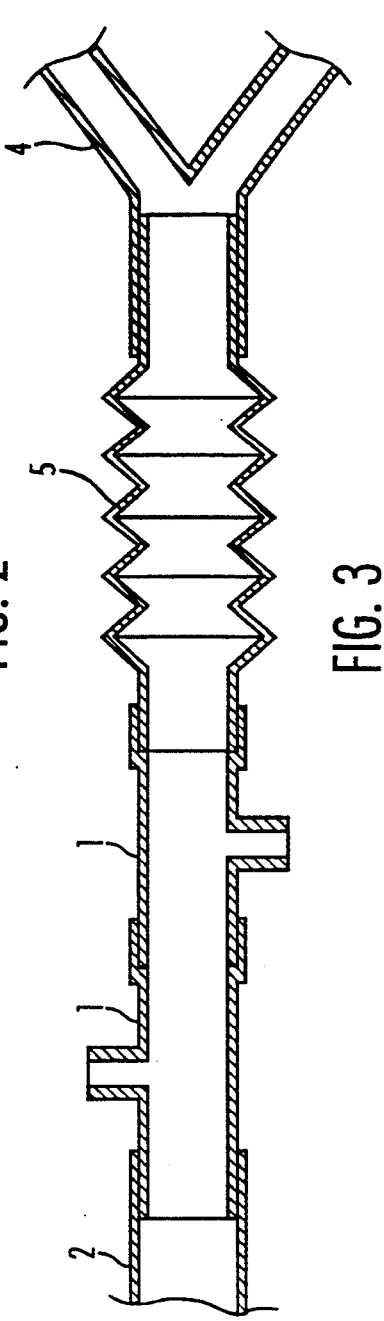

ANESTHESIA CONDUIT

BACKGROUND OF THE INVENTION

1. Field of the Invention

The present invention is directed to a connector from a tracheal tube to the anesthesia machine or respirator, herein referred to as an anesthesia conduit.

2. Description of the Related Art

Tracheal tubes are used to administer anesthetic gas during surgical procedures. Tracheal tubes are also used to provide oxygen from a respirator in order to assist patients who are experiencing breathing difficulty or weaning patients off respirators. The distal end of such a tube is positioned in the trachea of a patient, and hence the name. The distal end of one type of tracheal tube, a tracheostomy tube, may be inserted into the patient's trachea through an opening in the neck. The distal end of another type of tracheal tube, an endotracheal tube, may be inserted into the trachea through the patient's nose or mouth. The proximal end of either type of tracheal tube may be connected to a respirator or to an anesthesia circuit via a connector tube, thereby forming a path from the gas circuit to the patient's trachea.

During surgery, it is necessary to monitor a patient's respiration and vital signs. Respiration and vital sign monitoring entails measuring $CO_2$, $O_2$, $N_2O$ and anesthesic gas, in addition to other vital signs, such as pulse and blood pressure. Airway pressure and volume are also monitored. Such monitoring is typically performed by a respiratory gas monitor (RGM), such as is well known in the art. An example of one such monitor is the Ohmeda TM 5250 RGM. In order to connect the RGM to the path between the gas circuit and the patient, the RGM includes an adapter which is placed between the tracheal tube and the gas circuit. The RGM adapter includes a port which is connected to the RGM by a tube. As illustrated in FIG. 1, RGM adapters often include a male end and a female end so that the adapter 1 is arranged in series with the tracheal tube 2, connector tube 3 and gas circuit 4.

Suction may also be needed at some location between the tracheal tube 2 and the gas circuit in order to remove certain secretions from the lungs, mouth, etc. Thus, in addition to the RGM adapter, a suction adapter, having a port which can be used for suctioning tracheal and lung secretions is to be incorporated into the connector tube, RGM adapter and gas circuit.

In order to allow tubing from the gas circuit to be positioned without dislodging the tracheal tube, flexible tubing 5 is typically inserted between the connector tube 3 and the gas circuit 4. Such an arrangement is illustrated in FIG. 2. Additionally, as illustrated in FIG. 3, the flexible tubing 5, RGM adapter 1 and suction adapter 1 are connected in series (from up to three to four different connection sites) and used to form a pathway between the tracheal tube 2 and the gas circuit 4.

While useful for their intended purposes, there are a number of disadvantages inherent in placing RGM adapters, suction adapters and flexible tubing between a tracheal tube and a gas circuit. For example, each time one of these elements is added, an additional discontinuity, or junction, is formed between the tracheal tube and the gas circuit. Such junctions cause a number of problems during surgery; they are sources of disconnections and subsequent leaks. Disruption of delivery of oxygen and anesthesia agents to the patient creates a hazard to the patient and to operating room personnel, and contaminates the operating room environment. Accordingly, this path between the tracheal tube and the gas circuit must be continuously monitored for leaks and disconnections by the anesthesiologist or other personnel, particularly if the head and/or patient is turned in different directions during surgery. Thus, even when no leaks or disconnections occur at the junctions, the mere possibility of such an occurrence serves as a distraction.

Finally, the accuracy of the RGM depends upon the distance of the RGM adapter from the gas source, i.e. the patient's trachea. The closer the adapter is to the source, the more accurate the RGM's measurements. However, it is common for RGM adapters to be inadvertently positioned on the distal end of the connector tube, the point farthest from the patient. Such malpositioning needlessly increases the distance between the RGM adapter and the gas source, thereby decreasing the accuracy of the RGM's measurements.

SUMMARY OF THE DISCLOSURE

It is an object of the present invention to provide an improved apparatus and method of providing RGM ports, suction ports and flexible tubing between a gas circuit and a tracheal tube.

In accordance with preferred embodiments of the present invention, these and other objectives are achieved by providing an anesthesia conduit which is adapted to be placed between a tracheal tube and a gas circuit. The anesthesia conduit affords RGM and suction access, as well as positioning flexibility, and reduces the number of connections avoiding the sources of leaks and disconnections associated with the prior art.

In one embodiment of the present invention, the anesthesia conduit includes a substantially rigid longitudinally extending portion and a flexible portion integrally connected thereto.

In another aspect of the present invention, the longitudinally extending portion includes at least two ports, one of which is connected to an apparatus such as an RGM, the other provides a pathway for the insertion of a suction catheter. The port for the RGM is positioned adjacent to the proximal end of the tracheal tube, thereby facilitating accurate gas analysis.

BRIEF DESCRIPTION OF THE DRAWINGS

A detailed description of a preferred embodiment of the invention will be made with reference to the accompanying drawings.

FIG. 1 is a sectional view illustrating a tracheal tube, a connector tube, an adapter and a gas circuit connected in series.

FIG. 2 is a sectional view illustrating a tracheal tube, a connector tube, a flexible tube and a gas circuit connected in series.

FIG. 3 is a sectional view illustrating a tracheal tube, a pair of adapters, a flexible tube and a gas circuit connected in series.

DETAILED DESCRIPTION OF THE PREFERRED EMBODIMENT

Figure 4:
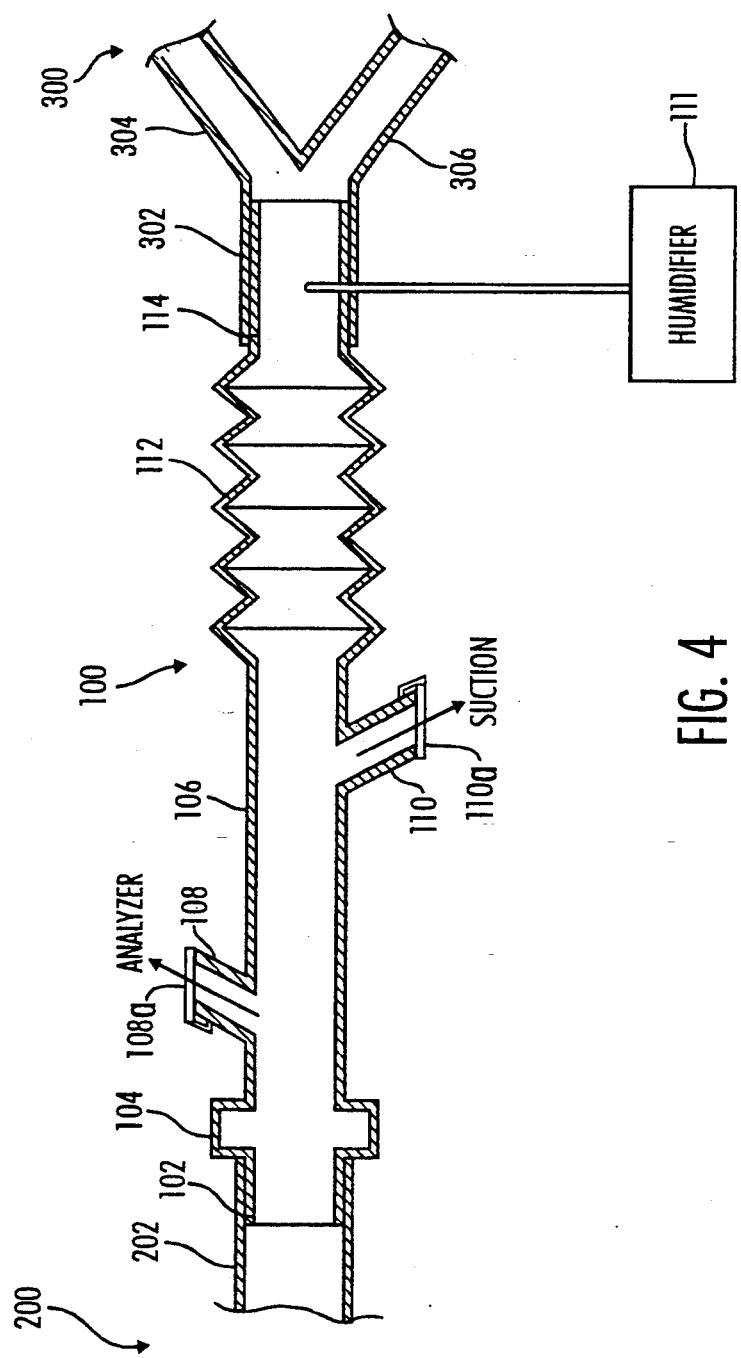
FIG. 4 is a sectional view of the anesthesia conduit in accordance with a preferred embodiment of the present invention.

The following is a detailed description of the best presently known mode of carrying out the invention. This description is not to be taken in a limiting sense, but is made merely for the purpose of illustrating general principles of embodiments of the invention. The scope of the invention is defined by the appended claims.

As illustrated for example in FIG. 4, the anesthesia conduit 100 includes an end portion 102 which is inserted into the proximal end 202 of a tracheal tube 200 such that the proximal end 202 abuts a raised portion 104 of the conduit 100. The dimension of the inner diameter of the end portion 102 may be manufactured in accordance with the outer diameter of the proximal end of the tracheal tube with which it is intended to be used. Alternatively, end portion 102 can be tapered so as to fit snugly into tracheal and/or endotracheal tubes of different internal diameters.

Extending from the raised portion 104 is a substantially rigid longitudinally extending portion 106 which includes ports 108 and 110. The ports 108 and 110 are, for example, respectively connected to an RGM and a suction source. The ports 108 and 110 may be respectively provided with caps 108a and 110a for sealing the ports when they are not in use. Ports 108 and 110 may also include a Luer Lock connector or other similar connector as is known in the art such that tubes can be secured to the port, as desired. The RGM connection port 108 should be located as close as is practicable to the proximal end 202 of the tracheal tube 200 in order to facilitate accurate gas analysis. Port 110 is configured such that a suction catheter can be inserted into tube 202 to remove lung and other secretions. The device 100 can also include a humidifier 111 as illustrated in FIG. 4.

In preferred embodiments, the longitudinally extending portion 106 merges with one end of a flexible portion 112, thereby forming a unitary article having a longitudinally extending portion and a flexible portion. The other end of the flexible portion 112 includes an end portion 114 that is configured to be inserted into the distal end 302 of a gas circuit 300, which itself may include hoses 304 and 306. In one embodiment a humidifier 111 is inserted in the circuit such that humidified gas is directed to the patient.

In accordance with the illustrated embodiment, the flexible portion 112 may be composed of corrugated plastic, e.g., polyethylene, silicone, PVC or other suitable material known to those of skill in the art. Additionally, metal and/or plastic wire or other suitable stiffening material known to those of skill in the art may be incorporated into the flexible portion 112 to increase its ability to maintain a shape into which it is bent thereby facilitating fixed positioning of the tracheal tube 200 and the hoses 304 and 306 during a surgical procedure. For example, portion 112 can be made of metal ribbing such that the desired configuration of the tube that is adjusted is retained in a selected position.

Although the present invention has been described in terms of a preferred embodiment above, numerous modifications and/or additions to the above-described preferred embodiment would be readily apparent to one skilled in the art. As can be seen, a direct flow path is provided by conduit 100 between the tracheal tube 200 and the gas circuit 300. Ports 108, 110 are also in fluid flow communication with conduit 100, and more particularly portion 106, in a manner such that the flow path between tube 200 and circuit 300 is not impeded. Further, since the elements are configured so as to eliminate the need for multiple connections, many problems associated with the prior art devices are eliminated. It is intended that the scope of the present invention extends to all apparent modifications and/or additions and that the scope of the present invention is limited solely by the claims set forth below.

We claim:

1. An external multi-function conduit device for connecting a gas circuit and a tracheal tube, which can be connected to a patient's head, to provide a gas flow path between the gas circuit and the tracheal tube, the device comprising:

a unitary conduit of sufficient length to operatively couple the gas circuit to the tracheal tube, the unitary conduit being formed by a plurality of integral portions that cannot be separated by movements of the patient's head, each of the integral portions performing a different function and all of the integral portions forming a continuous adaptive flow path along the length of conduit, the conduit including:

a flexible integral portion including a first end aperture adapted to be removably connected to the gas circuit; and a substantially rigid longitudinally extending integral portion that is integral with the flexible integral portion and having a second end aperture adapted to be removably connected to the tracheal tube, the longitudinally extending integral portion having a first port located adjacent said tracheal tube and adapted to be joined to a gas monitor.

2. The device of claim 1, wherein said first port includes a cap.

3. The device of claim 2, wherein said substantially rigid longitudinally extending integral portion includes a second port located adjacent said flexible integral portion, said second port configured such that a suction catheter can be inserted into the tracheal tube through the second port.

4. The device of claim 1, wherein the flexible integral portion is formed by a corrugated plastic material.

5. The device of claim 4, wherein the flexible integral portion further includes retaining means for retaining the flexible integral portion in a desired position.

6. The device of claim 5, wherein the retaining means is formed by metal ribbing.

7. An apparatus, comprising:

a gas circuit;

a tracheal tube; and an external unitary multi-function conduit for connecting the gas circuit and the tracheal tube, which can be connected to a patient's head, to provide a gas flow path between the gas circuit and the tracheal tube, the unitary conduit being of sufficient length to operatively couple the gas circuit to the tracheal tube, the unitary conduit being formed by a plurality of integral portions that cannot be separated by movements of the patient's head, each of the integral potions performing a different function and all of the integral portions forming a continuous adaptive flow path that is substantially free of leaks along the length of conduit, the conduit including:

a flexible integral portion having a first end aperture removable connected to the gas circuit; and a substantially rigid longitudinally extending integral portion that is integral with the flexible integral portion and having a second end aperture removably connected to the tracheal tube, the longitudinally extending integral portion extending a distance at least equal to a length of the flexible integral portion, and wherein the longitudinally extending integral portion includes a first port between the flexible integral portion and the second end aperture, said first port located adjacent said tracheal tube and adapted to be joined to a gas monitor.

8. The apparatus of claim 7, wherein said first port includes a cap.

9. The apparatus of claim 7, wherein said longitudinally extending integral portion includes a second port, said first port being located adjacent said tracheal tube and said second port located adjacent said flexible integral portion.

10. The apparatus of claim 7, wherein the flexible integral portion is formed by corrugated plastic.

11. The apparatus of claim 7, wherein the flexible integral portion includes retaining means for retaining the flexible integral portion in a desired position.

12. An external multi-function conduit device for connecting a gas circuit and a tracheal tube to provide a gas flow path between the gas circuit and the tracheal tube, the device comprising:
a unitary conduit formed from a single piece of material, the unitary conduit being formed by a plurality of integral portions that cannot be separated, each of the integral portions performing a different function and all of the integral portions forming a continuous adaptive flow path along the length of conduit, the conduit including:
a flexible integral portion formed from the single piece of material, the flexible integral portion including a first end adapted to be removably connected to the gas circuit; and
a substantially rigid longitudinally extending integral portion formed from the single piece of material and which is integral with the flexible integral portion and having a second end adapted to be removably connected to the tracheal tube, the longitudinally extending integral portion having a first port located adjacent said tracheal tube and adapted to be joined to a gas monitor.

13. The device of claim 12, wherein said first port includes a cap.

14. The device of claim 13, wherein said substantially rigid longitudinally extending integral portion includes a second port located adjacent said flexible integral portion, said second port configured such that a suction catheter can be inserted into the tracheal tube through the second port.

15. The device of claim 12, wherein the unitary conduit is formed by a plastic material.

16. The device of claim 15, wherein the flexible integral portion includes retaining means for retaining the flexible integral portion in a desired position.

17. The device of claim 16, wherein the retaining means is formed by metal ribbing.

18. The device of claim 12, wherein the longitudinally extending integral portion extends a distance at least equal to a length of the flexible integral portion.

* * * * *